(12) United States Patent
Hill

(10) Patent No.: US 7,850,989 B2
(45) Date of Patent: Dec. 14, 2010

(54) CRITICAL CARE FOR NEONATAL CALVES

(75) Inventor: T Mark Hill, Clayton, OH (US)

(73) Assignee: Provimi North America, Inc., Brookville, OH (US)

( * ) Notice: Subject to any disclaimer, the term of this patent is extended or adjusted under 35 U.S.C. 154(b) by 1482 days.

(21) Appl. No.: 10/702,406

(22) Filed: Nov. 6, 2003

(65) Prior Publication Data

US 2004/0253324 A1 Dec. 16, 2004

Related U.S. Application Data

(60) Provisional application No. 60/477,827, filed on Jun. 12, 2003.

(51) Int. Cl.
*A61K 9/00* (2006.01)
*A61K 31/70* (2006.01)

(52) U.S. Cl. .................. 424/442; 426/658; 514/23

(58) Field of Classification Search ............... 424/117, 424/679, 680, 439, 442; 514/59, 23; 426/658
See application file for complete search history.

(56) References Cited

U.S. PATENT DOCUMENTS

| | | | |
|---|---|---|---|
| 3,873,695 A | | 3/1975 | Pastre |
| 3,898,328 A * | | 8/1975 | Beigler et al. ............... 424/601 |
| 4,167,587 A * | | 9/1979 | Danforth ................ 426/250 |
| 4,418,091 A | | 11/1983 | Glas |
| 4,547,377 A * | | 10/1985 | Ogawa et al. ............... 426/268 |
| 4,600,585 A | | 7/1986 | Vitcenda et al. |
| 4,689,319 A | | 8/1987 | Phillips et al. |
| 5,038,396 A | | 8/1991 | Gjerlov |
| 5,128,167 A | | 7/1992 | De Laporte |
| 5,397,786 A * | | 3/1995 | Simone ..................... 514/300 |
| 5,635,199 A * | | 6/1997 | Trimbo et al. ............... 424/439 |
| 5,756,132 A | | 5/1998 | Rebhan |
| 5,785,990 A * | | 7/1998 | Langrehr ................... 424/442 |
| 6,033,689 A | | 3/2000 | Waterman et al. |
| 6,156,333 A | | 12/2000 | Langrehr |
| 6,465,032 B1 * | | 10/2002 | Hollar ....................... 426/506 |
| 2002/0176881 A1 * | | 11/2002 | Verlaan et al. ............... 424/439 |
| 2003/0064135 A1 * | | 4/2003 | Portman ..................... 426/72 |

FOREIGN PATENT DOCUMENTS

| | | |
|---|---|---|
| JP | 61289845 | 12/1986 |
| JP | 61289846 | 12/1986 |
| JP | 7118162 | 5/1995 |
| WO | WO 91/09536 | 7/1991 |
| WO | WO 95/28091 | 10/1995 |
| WO | WO 00/48474 | 8/2000 |

OTHER PUBLICATIONS

Webster's New World Dictionary, 3rd College Ed., Webster's New World Dictionary Publishing, p. 1067-1068 (1988).*

* cited by examiner

*Primary Examiner*—Johann R Richter
*Assistant Examiner*—Ali Soroush
(74) *Attorney, Agent, or Firm*—Jacox, Meckstroth & Jenkins

(57) ABSTRACT

A product and method for treating dehydration in neonatal calves. The product is administered to dehydrated calves during treatment, to the exclusion of milk replacers or electrolytes.

11 Claims, 1 Drawing Sheet

CRITICAL CARE FOR NEONATAL CALVES

CROSS-REFERENCE TO RELATED APPLICATION

This application is related to provisional patent application Ser. No. 60/477,827, filed Jun. 12, 2003, to which Applicants claim the benefit of the earlier filing date.

BACKGROUND OF THE INVENTION

1. Field of the Invention

This invention relates to calf raising and more particularly to a milk replacer and electrolyte for herd replacement calves.

2. Description of the Related Art

This invention deals specifically with the problem of dehydration of neonatal calves which can occur during transportation or in the course of scouring (diarrhea). Management of the calf that is scouring with bacterial enteritis is a major challenge. Previous management strategies have recommended removing milk from the scouring calf and feeding electrolytes. The logic was based on field observations that fecal output and fluid losses were reduced when the milk was removed.

SUMMARY OF THE INVENTION

It has been found that milk replacer (MR) should continue to be fed with 2-4 doses of electrolytes to provide enough energy and protein to maintain some level of growth. In extreme cases of calf scours, where the manure is watery with the appearance of no solids for over 24-36 hours, it has been believed that milk or MR should be removed and only electrolytes fed. Removing the milk or MR removes the lactose that feeds the bacteria and draws fluids into the gut, making scouring worse. Milk and MR also provide fat which may not be digested well in a scouring calf.

Calves under a week of age are often dehydrated upon arrival. It has been learned that better gains in health may be achieved in calves when only electrolytes are fed on arrival, as opposed to a milk replacer, a serum, plasma or whey product in all situations. A single effective product could eliminate the need to identify the severity of scouring before determining what management approach to take in the treatment protocol on a sick calf.

An objective of this product is to provide a source of nutrients to a calf
   a) that will effectively rehydrate,
   b) that provide for maintenance and growth, and
   c) that are not antagonistic to rehydration.

In accordance with this invention there is provided a product, hereinafter referred to as Critical Care® product, which is a milk replacer and electrolyte for bovine mammals and more particularly, herd replacement calves. Critical Care® is designed to be a complete source of nutrients and electrolytes for treating and reducing the likelihood of dehydration in calves less than three months of age and being fed a diet that is predominately milk or milk replacer. The Critical Care® product is particularly useful for treating calves which have been dehydrated through, for example, stress of transportation and upon arrival at their destination. A preferred dosage for a single arriving calf in a newly dehydrated state is about 0.45 to 0.55 pounds of Critical Care® product diluted in a total volume of about two quarts using water at a temperature of about 100 degrees Fahrenheit (to aid in dissolving and administration) and is given by bottle, bucket or drench. Once fed, neither milk nor milk replacer should be fed to the calf for six hours or until the next scheduled feeding in a two times per day feeding program.

The Critical Care® product can preferably be given to scouring calves in the amount of about 0.45 to 0.55 pounds diluted in a total volume of about two quarts using about 100 degree Fahrenheit water by bottle, bucket or drench. Such feeding should be done a minimum of three times during a 24 hour period, as needed, based on physical signs of dehydration and water loss. When manure consistency becomes firm (typically within 24 hours) feeding of the Critical Care® product may be discontinued, and the calves returned to their normal feeding schedule of milk or milk replacer. If the manure consistency is still loose (watery) the procedure should be repeated for another 24 hour period. The procedure may be again repeated as required. The calves are removed from their milk or milk replacer during their treatment by the Critical Care® product.

DESCRIPTION OF THE PREFERRED EMBODIMENT

Figure 1:
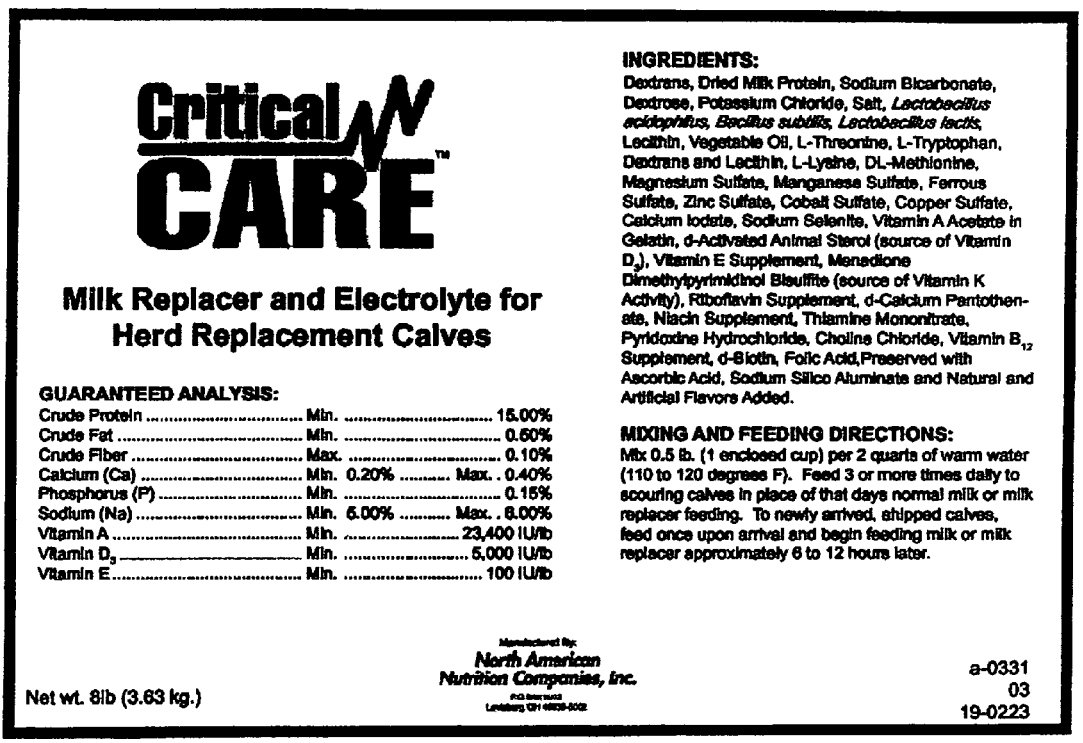
FIG. 1 is an illustration of a label for a product made in accordance with the invention.

In the preferred embodiment of the invention the Critical Care® product may have an ingredient composition and nutrient profile as set forth in Table I below.

Table I

TABLE I

| Ingredient | Percent |
|---|---|
| Maltodextrin | 39.80 |
| Whey protein concentrate 90% | 16.55 |
| Bicarbonate of soda | 15.00 |
| Dextrose | 15.00 |
| Potassium chloride | 5.00 |
| Salt | 2.60 |
| Lecithin (emulsifier) | 2.00 |
| Zeolite (anticaking agent) | 1.00 |
| L-lysine (amino acid) | .83 |
| Sodium saccharine (artificial sweetener) | .50 |
| DL-methionine (amino acid) | .39 |
| Vitamin and trace mineral premix | .34 |
| Sodium butyrate (flavor) | .34 |
| L-threonine (amino acid) | .24 |
| Artificial flavor | .20 |
| L-tryptophan (amino acid) | .11 |
| Microbial blend | .10 |

| Nutrient | Amount |
|---|---|
| Crude protein, % | 15.0 |
| Calcium, % | .3 |
| Phosphorus, % | .2 |
| Salt, % | 2.6 |
| Sodium, % | 5.5 |
| Chloride, % | 4.1 |
| Potassium, % | 2.7 |
| Selenium, ppm | .2 |
| Vitamin A, IU/lb | 23,400 |
| Vitamin D, IU/lb | 5,000 |
| Vitamin E, IU/lb | 100 |

The ingredients listed in Table I are added to a mixer, with those ingredients comprising 10% or more being added first. The remaining smaller inclusion rate ingredients are added last, excluding the artificial flavor and lecithin. The mixer is started and the artificial flavor is added, followed by lecithin.

The combined ingredients are packaged immediately after mixing. The package consists of a plastic liner filled with the product and tied with a twist-tie inside a sealed plastic pail. The finished package is marked with the trademark CRITICAL CARE®. FIG. 1 depicts a typical label.

The Critical Care® product is rehydrated prior to being fed to calves. An alkalizing (i.e. bicarbonate of soda) agent is needed to correct the metabolic pH of the calf to allow efficient use of nutrients. Sodium (Na) and potassium (K) are needed as electrolytes to rehydrate. Na and K have been lost from the calf during dehydration. A source of nutrients, like glucose or dextrans, is used to facilitate the transport of the Na and K from the gut into the bloodstream. Research in the public domain indicate that a composition of an effective electrolyte administered orally should be approximately 50 to 70% glucose and/or dextrans, 12-18% bicarbonate of soda, 5-6% total Na, and 2.5-3.0% total K. The proportions of these nutrients to each other in a product are important. The actual percent in the product is not. The Critical Care® product contains approximately 54.8% dextrans, 15% bicarbonate of soda, 5.5% Na, and 2.7% K.

For rehydration approximately one quart of 100 degree Fahrenheit water is added to a pail or bottle and about 0.5 pounds of The Critical Care® product is sprinkled on the surface of the water and mixed into the water by vigorously stirring with a whisk or similar stirring device. Then the volume of the solution is increased to two quarts by adding more 100 degree Fahrenheit water. This mixture is then fed to a calf by bucket or bottle. If the calf refuses to drink or is too weak to consume it, it is administered by drenching.

The Critical Care® product is designed to be a complete source of nutrients and electrolytes for dehydrated calves three months of age or less and being fed a diet that is predominately milk or milk replacer. As noted above, calf dehydration may be brought about by the stress of transportation or by scouring. When the condition is brought about by transportation, the Critical Care® product should be administered upon arrival of the calf at its destination. This treatment upon arrival involves feeding about 0.5 pounds of the Critical Care® product in a total volume of two quarts using 100 degree Fahrenheit water by bottle, bucket or drench. Neither milk nor milk replacer should be fed to the calf for 6 hours or until the next scheduled feeding in a two times a day feeding program. In those cases where the dehydration results from scouring (diarrhea) the calves should not be given their milk or milk replacer for a period of 24 hours. Instead they should be fed about 0.5 pounds of the Critical Care® product diluted in a total volume of two quarts using 100 degree Fahrenheit water by bucket, bottle or drench a minimum of three times during the 24 hour period (administer one to two feedings of the Critical Care® product within the 24 hour period, if needed, based upon physical signs of dehydration and water loss. When manure consistency becomes firm (typically within 24 hours), discontinue feeding the Critical Care® product and return calves to the normal feeding schedule of milk or milk replacer. If the manure consistency is still loose (watery) after 24 hours, repeat for another 24-hour period the administration of three or more doses of the Critical Care® product without feeding milk or milk replacer. Again, if the manure consistency is still loose (watery) after the second 24-hour period, repeat for another 24 hour the administration of three or more doses of tee Critical Care® product without feeding milk or milk replacer.

Crude protein and energy from carbohydrates and/or fat are needed for maintenance and growth. For example, cow's milk is approximately 22% crude protein, 26% fat, and 40% lactose (carbohydrate) on a dry basis and consumed/fed at approximately 1 lb of dry matter daily. In a dehydrated calf, excessive lactose will serve to hold Na and K in the gut and counteract Na and K absorption into the bloodstream. It will even serve to worsen dehydration by promoting scouring (excessive watery feces). Fat digestion is often very poor in a scouring calf and its utilization for energy is inefficient. Dextrose and glucose, commonly used energy sources in electrolytes, can also work like lactose to create a high gut osmolarity to hold Na and K in the gut and counteract Na and K absorption into the bloodstream. The Critical Care® product provides crude protein via a milk protein source that is virtually free of lactose and fat (whey protein concentrate 90%). The Critical Care® product contains limited dextrose (15%) and predominately maltodextrin (39.8%) as its sources of needed dextrans/carbohydrates. Maltodextrans have a much lower osmolarity than dextrose, glucose, and lactose. The Critical Care® product contains no added fat other than the limited soy oil that is a part of the lecithin needed to emulsify the product. The Critical Care® product contains less than about 1% lactose and less than about 1% fat. The three recommended doses of the Critical Care® product provide a similar amount of protein (slightly more) and energy (slightly less) as what the calf normally receives via milk.

Our research shows that the Critical Care® product is effective. In shipped, dehydrated calves gains were better and medical treatments were lower (P<0.1) for calves fed the Critical Care® product verses a traditional electrolyte that provided a similar amount of bicarbonate of soda, Na and K as the Critical Care® product provided. The P value is a statistical probability indicating that these differences between the two treatments are less than 0.1 or less than 10% likely to occur due to chance (or greater than 90% due to the experimental treatment of using the Critical Care® product instead of the traditional electrolyte). The SEM (standard error of the mean) were low in these trials compared to similar research published in the literature using calves from a few days old up to 3 months of age, indicating good experimental control of the trials. The low P values and low SEM's give us excellent confidence in the experimental data.

The effectivity of the Critical Care® product, administered as described above has been demonstrated by four research trials involving 200 calves under a week of age. The results of Trials 1-4 are summarized in Tables II-V. These four trials were based upon the hypothesis that dehydrated calves need electrolytes and water first, a rapid source of energy second, and protein third. Two nutrient profiles typical of the U.S. market and a combination of milk protein concentrate (90% protein, ~1% lactose) and electrolytes were formulated to evaluate this hypothesis.

Feeding high lactose feeds could pull water into the gut and high fat feeds may be poorly digested in starved calves, increasing scouring. The assigned treatments were diluted to about 1.9 liters of volume with warm water and fed the afternoon of arrival only and were: A) 113 g of electrolyte A, B 113 g of electrolyte B, C) 226 g of a combination of electrolyte B with milk protein. Treatment A was fed only in trial 1.

Calves arrived after a 10-hour transport. Treatments were administered between 1600 and 1700 hours on the day of arrival and free-choice water was offered in pails. The following morning calves were fed MR and offered starter. Calves were housed in individual pens bedded with straw. Calves had access to clean fresh water and dry starter feed (with 0.0025% decoquinate) at all times. Milk replacers (with 0.005% decoquinate) were fed twice daily. The nursery was naturally ventilated with no heat. Starter feed offered and refused was weighed daily. Feces were scored daily using a 1 to 5 scale with 1 being normal and 5 being watery. Medical treatments were recorded daily. Calves were weighed on-arrival (in Trial 1 only), 21 hours later (used as our initial weight and to calculate gains), and weekly, thereafter. Body condition score (1 being thin and 5 being obese) and hip widths were measured initially and at 6 and 7 weeks. Calves were weaned at 6 weeks. Data from trials 3 and 4 were analyzed as a completely randomized design (block was row in the barn).

Initial calf body weight averaged 41 to 43 kg in the 4 trials. For Trial 1, the initial 21-hour weight change was greatest (P<0.1) for calves offered treatment C (1,005 g, 1,284 g, 2,088 g for treatments A, B, C, respectively). Cumulative daily gains were greatest (P<0.05) for calves fed treatment C for all weeks. Weekly gains were greatest (P<0.1) for calves fed treatment C for weeks 1, 5, and 7 and numerically greater for calves fed treatment C each week except weeks 2 and 8. Starter intake did not differ with treatment but appeared numerically greater for calves fed treatment C. Cumulative feed efficiency was best (P<0.05) for calves fed treatment C for weeks 3 to 8. Cumulative medical days and fecal scores tended to favor calves fed treatment C. Cumulative medical days were significantly lower (P<0.1) for calves fed treatment C by weeks 7 and 8. There were no differences (P>0.1) between treatment A and B.

In trial 2, cumulative daily gains (P<0.01) and starter intake (P<0.1) were greatest for calves fed treatment C for all weeks. Cumulative feed efficiency was best for calves fed treatment C in weeks 5 through 8 (P<0.05). Cumulative body condition score change and hip width change were greatest (P<0.06) for calves fed treatment C through 6 and 8 weeks, respectively. There were few differences in fecal scores and medical treatments; however, cumulative weekly medical days over the entire 8 weeks were lowest (P<0.05) for calves fed treatment C.

In trial 3, daily gains were greatest (P<0.01) for calves fed treatment C during the first week of the trial and tended (P>0.1) to favor calves fed treatment C for all weeks. Cumulative feed efficiency was best for calves fed treatment C in weeks 5 through 8 (P<0.08). Cumulative fecal score and cumulative abnormal fecal scores were best (P<0.1) for calves fed treatment B for all weeks.

In trial 4, cumulative daily gains were greatest (P<0.1) for calves fed treatment C during the first 3 weeks of the trial and tended (P>0.1) to favor calves fed treatment C for all weeks. There were little differences in medical treatments or fecal scores between treatments.

Feeding treatment C on-arrival, improved calf gains in the first week of all trials and improved cumulative gains for all weeks in trials 1 and 2. This was the trend for trials 3 and 4, as well. Cumulative feed efficiency was improved in weeks 5 through 8 in trials 1, 2, and 3.

Over the course of 4 research trials 16 calves with watery scours were randomly treated with either 1) an effective electrolyte or 2) the Critical Care® product, which is a milk protein combined with electrolytes without lactose or fat. Watery scours were quantified using a fecal scoring system with a scale of 1 to 5. A fecal score of 1 was normal, firm manure. A fecal score of 4 or 5 was watery with some to no solid material visible. The calves used in the research had been transported from 10 hours away. In these trials, as in most of our trials, many of the calves developed bacterial scours by the 7th day after arrival. In these trials, the calves with severe scours were treated with electrolytes and antibiotics during the week after arrival. Calves were weighed on arrival and weekly thereafter. Scour scores and medical treatments were recorded daily. A treatment protocol outlined by a consulting veterinarian was followed which included the three doses of electrolytes daily for calves with fecal scores over 4 and antibiotics until fecal scores improved to less than a score of 3. Calves assigned to the electrolyte treatment received three doses of electrolyte along with their MR feedings. Calves assigned to the Critical Care® product treatment received 3 doses of the Critical Care® product and did not receive their MR that day. All of the calves received a common 20% all milk protein, 20% fat MR containing 0.005% decoquinate and a common 18% protein starter containing 0.0025% decoquinate. Data were analyzed as a completely randomized block design (block was trial).

Data for the scouring calves are summarized in Tables VI and VII. Daily gain, fecal scores, and antibiotic treatments for both treatment groups were similar in week 1. Daily gains during week 2 were greater (P<0.10) for calves fed the Critical Care® product vs. the electrolyte group. Similarly, the improvement in fecal score from week 1 to week 2 was twice as great (P<0.10) for calves treated with the Critical Care® product compared to the calves treated with the electrolyte. Six of the eight calves in the electrolyte treatment group required antibiotic treatments during week two (average 2.25 treatments per calf) compared to (P<0.02) only two of the eight calves in the Critical Care® product treatment group (averaged 0.25 treatments per calf). Four of the eight calves in the electrolyte group required a second day of three electrolyte doses because the severe scouring persisted compared to (P<0.01) none of the calves in the Critical Care® product group (4.5 vs 3.0 doses).

Feeding calves 3 doses of the Critical Care® product and removing their MR for 1 day resulted in similar to better performance and fewer antibiotic and electrolyte treatments than feeding 3 doses of a good quality electrolyte with MR.

TABLE VI

Means for various measurements after scouring (diarrhea) calves were fed an electrolyte or the Critical Care ® product.

| | Electrolyte | Critical Care ® product | SEM | P Value |
|---|---|---|---|---|
| Initial body weight, kg | 42.7 | 40.3 | 3.8 | 0.45 |
| Week 1 Daily Gain, g | −28.6 | −53.1 | 65.7 | 0.80 |
| Week 2 Daily Gain, g | −37.7 | 89.0 | 47.9 | 0.10 |
| Average of Week 1 and 2 Daily Gain, | −33.1 | 17.7 | 54.5 | 0.53 |
| Week 2 minus Week 1 Daily Gain, g | −9.1 | 142.1 | 37.0 | 0.02 |
| Week 1 Fecal Score | 2.65 | 2.78 | 0.0758 | 0.26 |
| Week 2 Fecal Score | 2.37 | 2.17 | 0.1516 | 0.38 |
| Average of Week 1 and 2 Fecal Score | 2.51 | 2.48 | 0.1022 | 0.86 |
| Week 2 minus Week 1 Fecal Score | −0.29 | −0.61 | 0.1258 | 0.10 |
| Week 1 Antibiotic Treatments | 4.63 | 4.25 | 0.2517 | 0.32 |
| Week 2 Antibiotic Treatments | 2.25 | 0.25 | 0.4640 | 0.02 |
| Total Antibiotic Treatments | 6.88 | 4.50 | 0.6776 | 0.04 |
| Total Electrolyte Treatments | 4.5 | 3.0 | 0.3333 | 0.01 |

TABLE VII

Daily gains (g) of calves fed the Critical Care ® product (Trt C) or two common electrolytes (Trt A and B) on arrival after a 10-hour shipment during three subsequent time periods in four trials.

| Trial | 1 | | | 2 | | 3 | | 4 | |
|---|---|---|---|---|---|---|---|---|---|
| Weeks | Trt A | Trt B | Trt C | Trt B | Trt C | Trt B | Trt C | Trt B | Trt C |
| 0–1 | −99 | −101 | 154[a] | −189 | 135[a] | −25 | 147[a] | 91 | 278[a] |
| 0–6 | 381 | 400 | 467[a] | 301 | 426[a] | 379 | 402 | 411 | 430 |
| 0–8 | 476 | 518 | 579[a] | 422 | 551[a] | 502 | 543 | 522 | 532 |

[a]Treatment C was greater than treatments A and/or B (P < .05) within specific trial and period.
(Treatment - Trt)

Research is continuing in the evaluation of the Critical Care® product. This continuing research has been conducted upon transported, dehydrated calves that typically have not yet been attacked by the bacteria or virus. This research model is good to use since it does not complicate the experiment with the challenge of the bacteria or virus. The ability of the product to rehydrate and promote growth is tested and the confounded factors of how long the attacking bacteria or virus has not been present.

Tables II-V:

TABLE II

LS Treatment means by week for calves fed three different initial electrolytes in Trial 1.

| | A) Elec A | B) Elec B | C) MP/ Elec B | SEM | P-Value[a] |
|---|---|---|---|---|---|
| Weight gain from arrival to initial weighing, g | | | | | |
| 21 hour period | 1,005.12 | 1,284.34 | 2,088.19 | 104 | 0.0987 |
| Average daily gain, g | | | | | |
| 1 | −99.23 | −101.97 | 154.31 | 37.1 | 0.0000 |
| 2 | 115.43 | 0.68 | 77.76 | 57.4 | 0.3258 |
| 3 | 412.70 | 505.78 | 529.34 | 58.9 | 0.3376 |
| 4 | 579.55 | 575.70 | 598.19 | 54.5 | 0.9503 |
| 5 | 622.08 | 718.26 | 734.67 | 35.6 | 0.0607 |
| 6 | 659.75 | 702.91 | 711.99 | 46.5 | 0.6957 |
| 7 | 602.24 | 777.26 | 933.53 | 98.6 | 0.0690 |
| 8 | 921.38 | 968.59 | 898.70 | 71.1 | 0.7584 |
| Average daily gain cumulative, g | | | | | |
| 1 | −99.23 | −101.97 | 154.31 | 37.1 | 0.0000 |
| 2 | 8.10 | −50.65 | 116.03 | 34.7 | 0.0036 |
| 3 | 142.97 | 134.83 | 253.80 | 32.7 | 0.0193 |
| 4 | 252.11 | 245.05 | 339.90 | 24.0 | 0.0104 |
| 5 | 326.11 | 339.69 | 418.85 | 22.1 | 0.0090 |
| 6 | 381.71 | 400.23 | 467.71 | 22.3 | 0.0211 |
| 7 | 413.22 | 454.09 | 534.25 | 28.6 | 0.0141 |
| 8 | 476.74 | 518.40 | 579.81 | 27.7 | 0.0381 |
| Average daily starter intake cumulative, g | | | | | |
| 1 | 28.01 | 16.21 | 30.96 | 6.45 | 0.2064 |
| 2 | 61.41 | 48.86 | 66.57 | 11.1 | 0.4783 |
| 3 | 105.58 | 100.87 | 119.90 | 13.9 | 0.5859 |
| 4 | 178.19 | 179.77 | 195.33 | 18.2 | 0.7584 |
| 5 | 270.10 | 283.94 | 305.11 | 22.5 | 0.5449 |
| 6 | 372.03 | 398.54 | 425.19 | 26.4 | 0.3696 |
| 7 | 529.16 | 580.46 | 620.34 | 33.6 | 0.1681 |
| 8 | 723.28 | 778.32 | 819.44 | 40.2 | 0.2470 |
| Weekly starter intake, g | | | | | |
| 1 | 196.06 | 113.47 | 216.69 | 45.1 | 0.2064 |
| 2 | 663.69 | 570.58 | 715.31 | 120 | 0.6644 |
| 3 | 1,357.38 | 1,434.21 | 1,586.00 | 172 | 0.6356 |
| 4 | 2,772.19 | 2,915.42 | 2,951.31 | 256 | 0.8710 |
| 5 | 4,464.25 | 4,904.26 | 5,209.50 | 313 | 0.2484 |
| 6 | 6,171.56 | 6,800.58 | 7,179.19 | 383 | 0.1807 |
| 7 | 10,303.69 | 11,703.95 | 12,538.88 | 635 | 0.0508 |
| 8 | 14,574.75 | 15,143.53 | 15,492.00 | 712 | 0.6571 |
| Starter intake cumulative, g | | | | | |
| 1 | 196.06 | 113.47 | 216.69 | 45.1 | 0.2064 |
| 2 | 859.75 | 684.05 | 932.00 | 155 | 0.4783 |
| 3 | 2,217.13 | 2,118.26 | 2,518.00 | 291 | 0.5859 |
| 4 | 4,989.31 | 5,033.68 | 5,469.31 | 508 | 0.7584 |
| 5 | 9,453.56 | 9,937.95 | 10,678.81 | 788 | 0.5449 |
| 6 | 15,625.13 | 16,738.53 | 17,858.00 | 1107 | 0.3696 |
| 7 | 25,928.81 | 28,442.47 | 30,396.88 | 1647 | 0.1681 |
| 8 | 40,503.56 | 43,586.00 | 45,888.88 | 2253 | 0.2470 |
| Feed efficiency cumulative (Starter and Milk Replacer/Gain) | | | | | |
| 1 | 5.84 | −1.72 | 0.31 | 5.40 | 0.5694 |
| 2 | 3.75 | 1.81 | −0.76 | 4.62 | 0.7809 |
| 3 | 32.00 | −13.07 | 2.28 | 12.5 | 0.0347 |
| 4 | 2.78 | 3.06 | 1.78 | 0.27 | 0.0026 |

TABLE II-continued

LS Treatment means by week for calves fed three different initial electrolytes in Trial 1.

| | A) Elec A | B) Elec B | C) MP/ Elec B | SEM | P-Value[a] |
|---|---|---|---|---|---|
| 5 | 2.33 | 2.27 | 1.67 | 0.11 | 0.0001 |
| 6 | 2.21 | 2.17 | 1.75 | 0.09 | 0.0007 |
| 7 | 2.43 | 2.18 | 1.86 | 0.14 | 0.0240 |
| 8 | 2.30 | 2.18 | 2.00 | 0.08 | 0.0341 |
| Weekly medical days | | | | | |
| 1 | 4.06 | 4.11 | 3.69 | 0.19 | 0.2340 |
| 2 | 0.44 | 0.79 | 0.50 | 0.19 | 0.3366 |
| 3 | 0.44 | 0.37 | 0.13 | 0.19 | 0.4804 |
| 4 | 0.56 | 0.47 | 0.06 | 0.25 | 0.3355 |
| 5 | 1.06 | 0.47 | 0.50 | 0.22 | 0.1081 |
| 6 | 0.63 | 0.58 | 0.38 | 0.22 | 0.6849 |
| 7 | 0.75 | 0.42 | 0.00 | 0.19 | 0.0263 |
| 8 | 0.19 | 0.11 | 0.25 | 0.14 | 0.7486 |
| Fecal score (1 = normal, 5 = watery) | | | | | |
| 1 | 2.77 | 2.72 | 2.73 | 0.05 | 0.7932 |
| 2 | 2.29 | 2.37 | 2.17 | 0.07 | 0.1104 |
| 3 | 1.96 | 1.92 | 1.87 | 0.08 | 0.7590 |
| 4 | 1.81 | 1.75 | 1.63 | 0.07 | 0.1920 |
| 5 | 1.63 | 1.47 | 1.41 | 0.10 | 0.2729 |
| 6 | 1.42 | 1.35 | 1.31 | 0.08 | 0.6579 |
| 7 | 1.37 | 1.40 | 1.21 | 0.08 | 0.2058 |
| 8 | 1.18 | 1.34 | 1.23 | 0.08 | 0.3214 |
| Weekly medical days cumulative | | | | | |
| 1 | 4.06 | 4.11 | 3.69 | 0.19 | 0.2340 |
| 2 | 4.50 | 4.89 | 4.19 | 0.29 | 0.2038 |
| 3 | 4.94 | 5.26 | 4.31 | 0.41 | 0.2344 |
| 4 | 5.50 | 5.74 | 4.38 | 0.49 | 0.1141 |
| 5 | 6.56 | 6.21 | 4.88 | 0.58 | 0.1017 |
| 6 | 7.19 | 6.79 | 5.25 | 0.69 | 0.1170 |
| 7 | 7.94 | 7.21 | 5.25 | 0.74 | 0.0375 |
| 8 | 8.13 | 7.32 | 5.50 | 0.78 | 0.0608 |
| Fecal score cumulative (1 = normal, 5 = watery) | | | | | |
| 1 | 2.77 | 2.72 | 2.73 | 0.05 | 0.7932 |
| 2 | 2.53 | 2.55 | 2.45 | 0.05 | 0.3325 |
| 3 | 2.34 | 2.34 | 2.26 | 0.05 | 0.4543 |
| 4 | 2.21 | 2.19 | 2.10 | 0.05 | 0.2770 |
| 5 | 2.09 | 2.05 | 1.96 | 0.05 | 0.2249 |
| 6 | 1.98 | 1.93 | 1.85 | 0.05 | 0.2369 |
| 7 | 1.89 | 1.85 | 1.76 | 0.05 | 0.1558 |
| 8 | 1.80 | 1.79 | 1.70 | 0.04 | 0.1721 |
| Total abnormal fecal scores (abnormal >2 fecal score) | | | | | |
| 1 | 6.50 | 6.53 | 6.38 | 0.18 | 0.8076 |
| 2 | 3.44 | 4.58 | 3.06 | 0.49 | 0.0683 |
| 3 | 1.00 | 1.21 | 1.13 | 0.38 | 0.9185 |
| 4 | 0.81 | 0.53 | 0.56 | 0.21 | 0.5786 |
| 5 | 0.75 | 0.21 | 0.13 | 0.19 | 0.0489 |
| 6 | 0.31 | 0.21 | 0.19 | 0.13 | 0.7688 |
| 7 | 0.56 | 0.47 | 0.31 | 0.23 | 0.7360 |
| 8 | 0.13 | 0.68 | 0.13 | 0.23 | 0.1275 |
| Total abnormal fecal scores cumulative (abnormal >2 fecal score) | | | | | |
| 1 | 6.50 | 6.53 | 6.38 | 0.18 | 0.8076 |
| 2 | 9.94 | 11.11 | 9.44 | 0.53 | 0.0630 |
| 3 | 10.94 | 12.32 | 10.56 | 0.75 | 0.1924 |
| 4 | 11.75 | 12.84 | 11.13 | 0.87 | 0.3386 |
| 5 | 12.50 | 13.05 | 11.25 | 0.95 | 0.3719 |
| 6 | 12.81 | 13.26 | 11.44 | 1.00 | 0.3910 |
| 7 | 13.38 | 13.74 | 11.75 | 1.06 | 0.3611 |
| 8 | 13.50 | 14.42 | 11.88 | 1.10 | 0.2410 |
| Body condition score changes (1 = thin, 5 = obese) | | | | | |
| Initial Score | 2.09 | 2.13 | 2.15 | 0.04 | 0.5514 |
| Change 0 to 2 wk | −0.09 | −0.18 | −0.10 | 0.04 | 0.2022 |
| Change 0 to 4 wk | 0.13 | −0.01 | 0.14 | 0.04 | 0.0136 |
| Change 0 to 6 wk | 0.22 | 0.18 | 0.21 | 0.05 | 0.8567 |
| Change 0 to 8 wk | 0.39 | 0.41 | 0.40 | 0.06 | 0.9741 |
| Change 2 to 4 wk | 0.22 | 0.17 | 0.25 | 0.04 | 0.3837 |

TABLE II-continued

LS Treatment means by week for calves fed three different initial electrolytes in Trial 1.

| | A) Elec A | B) Elec B | C) MP/ Elec B | SEM | P-Value[a] |
|---|---|---|---|---|---|
| Change 4 to 6 wk | 0.09 | 0.20 | 0.07 | 0.05 | 0.1977 |
| Change 6 to 8 wk | 0.17 | 0.22 | 0.18 | 0.06 | 0.7787 |
| Hip width changes, cm | | | | | |
| Initial Width | 17.30 | 17.36 | 17.20 | 0.19 | 0.8467 |
| Change 0 to 2 wk | 0.28 | 0.30 | 0.47 | 0.09 | 0.2992 |
| Change 0 to 4 wk | 0.80 | 0.78 | 1.14 | 0.11 | 0.0461 |
| Change 0 to 6 wk | 2.36 | 2.28 | 2.69 | 0.17 | 0.1760 |
| Change 0 to 8 wk | 3.63 | 3.89 | 4.56 | 0.22 | 0.0120 |
| Change 2 to 4 wk | 0.52 | 0.47 | 0.67 | 0.09 | 0.2340 |
| Change 4 to 6 wk | 1.56 | 1.50 | 1.55 | 0.10 | 0.8898 |
| Change 6 to 8 wk | 1.27 | 1.62 | 1.88 | 0.12 | 0.0034 |

[a]When P Values were lower than .1, treatment C was different than treatments A and B.

TABLE III

LS Treatment means by week for calves fed two different electrolytes in Trial.

| | B) Elec B | C) Elec C | SEM | P-Value[a] |
|---|---|---|---|---|
| Average daily gain, g | | | | |
| 1 | −189.46 | 135.00 | 56.1 | 0.0002 |
| 2 | 201.22 | 328.84 | 32.6 | 0.0081 |
| 3 | 304.15 | 310.85 | 35.7 | 0.8924 |
| 4 | 459.31 | 566.47 | 47.1 | 0.1111 |
| 5 | 583.64 | 736.93 | 45.4 | 0.0207 |
| 6 | 451.63 | 479.63 | 49.5 | 0.6869 |
| 7 | 720.55 | 804.62 | 58.5 | 0.3088 |
| 8 | 853.04 | 1,043.56 | 111 | 0.2150 |
| Average daily gain cumulative, g | | | | |
| 1 | −189.46 | 135.00 | 56.1 | 0.0002 |
| 2 | 5.88 | 231.92 | 38.1 | 0.0001 |
| 3 | 104.89 | 258.50 | 31.0 | 0.0011 |
| 4 | 193.50 | 335.49 | 29.1 | 0.0013 |
| 5 | 271.53 | 415.78 | 28.7 | 0.0010 |
| 6 | 301.54 | 426.42 | 28.7 | 0.0036 |
| 7 | 361.40 | 480.45 | 29.1 | 0.0058 |
| 8 | 422.97 | 551.08 | 30.0 | 0.0042 |
| Cumulative average daily starter intake, g | | | | |
| 1 | 35.81 | 63.01 | 10.4 | 0.0672 |
| 2 | 92.06 | 142.09 | 16.9 | 0.0411 |
| 3 | 165.82 | 217.10 | 21.6 | 0.0966 |
| 4 | 246.82 | 311.03 | 25.3 | 0.0771 |
| 5 | 336.41 | 418.21 | 29.3 | 0.0523 |
| 6 | 421.92 | 510.26 | 33.8 | 0.0688 |
| 7 | 586.17 | 687.48 | 39.5 | 0.0737 |
| 8 | 741.19 | 869.42 | 45.3 | 0.0495 |
| Weekly starter intake, g | | | | |
| 1 | 250.69 | 441.08 | 72.8 | 0.0672 |
| 2 | 1,039.28 | 1,546.12 | 180 | 0.0507 |
| 3 | 2,193.45 | 2,569.91 | 236 | 0.2590 |
| 4 | 3,428.77 | 4,149.73 | 295 | 0.0883 |
| 5 | 4,863.23 | 5,928.55 | 374 | 0.0481 |
| 6 | 5,946.32 | 6,793.54 | 446 | 0.1812 |
| 7 | 11,001.71 | 12,255.80 | 582 | 0.1305 |
| 8 | 12,786.72 | 14,996.30 | 738 | 0.0383 |

LS Treatment means by week for calves fed two different electrolytes in Trial 2 (cont.).

| | B) Elec B | C) Elec C | SEM | P-Value[a] |
|---|---|---|---|---|
| Starter intake cumulative, g | | | | |
| 1 | 250.69 | 441.08 | 72.8 | 0.0672 |
| 2 | 1,288.81 | 1,989.19 | 237 | 0.0411 |
| 3 | 3,482.26 | 4,559.10 | 453 | 0.0966 |
| 4 | 6,911.03 | 8,708.83 | 709 | 0.0771 |
| 5 | 11,774.26 | 14,637.38 | 1024 | 0.0523 |
| 6 | 17,720.58 | 21,430.92 | 1419 | 0.0688 |
| 7 | 28,722.29 | 33,686.72 | 1934 | 0.0737 |
| 8 | 41,506.90 | 48,687.49 | 2535 | 0.0495 |
| Feed efficiency cumulative (Starter and Milk Replacer/Gain) | | | | |
| 1 | 3.96 | 2.75 | 4.37 | 0.8422 |
| 2 | 0.73 | 3.30 | 1.79 | 0.3106 |
| 3 | 5.07 | 3.61 | 5.52 | 0.8480 |
| 4 | 7.00 | 2.74 | 1.14 | 0.0108 |
| 5 | 3.48 | 2.29 | 0.26 | 0.0026 |
| 6 | 3.13 | 2.47 | 0.17 | 0.0092 |
| 7 | 2.79 | 2.39 | 0.11 | 0.0113 |
| 8 | 2.61 | 2.33 | 0.10 | 0.0454 |
| Weekly medical days | | | | |
| 1 | 3.92 | 3.65 | 0.20 | 0.3463 |
| 2 | 0.70 | 0.74 | 0.33 | 0.9247 |
| 3 | 0.99 | 0.76 | 0.30 | 0.5903 |
| 4 | 0.22 | 0.21 | 0.13 | 0.9383 |
| 5 | 1.02 | 0.33 | 0.24 | 0.0496 |
| 6 | 0.75 | 0.63 | 0.31 | 0.7801 |
| 7 | 0.34 | 0.36 | 0.14 | 0.9251 |
| 8 | 1.37 | 0.38 | 0.47 | 0.1287 |
| Fecal score (1 = normal, 5 = watery) | | | | |
| 1 | 2.71 | 2.69 | 0.07 | 0.8731 |
| 2 | 2.48 | 2.39 | 0.05 | 0.1772 |
| 3 | 1.99 | 2.02 | 0.05 | 0.7490 |
| 4 | 1.54 | 1.81 | 0.17 | 0.2377 |
| 5 | 1.46 | 1.55 | 0.11 | 0.5511 |
| 6 | 1.31 | 1.30 | 0.09 | 0.9420 |
| 7 | 1.21 | 1.38 | 0.08 | 0.1370 |
| 8 | 1.16 | 1.33 | 0.07 | 0.0713 |
| Weekly medical days cumulative | | | | |
| 1 | 3.92 | 3.65 | 0.20 | 0.3463 |
| 2 | 4.64 | 4.37 | 0.28 | 0.5015 |
| 3 | 5.63 | 5.13 | 0.37 | 0.3357 |
| 4 | 5.85 | 5.34 | 0.39 | 0.3495 |
| 5 | 6.87 | 5.67 | 0.48 | 0.0822 |
| 6 | 7.62 | 6.31 | 0.70 | 0.1825 |
| 7 | 7.97 | 6.66 | 0.68 | 0.1725 |
| 8 | 9.37 | 7.01 | 0.70 | 0.0212 |
| Fecal score cumulative (1 = normal, 5 = watery) | | | | |
| 1 | 2.71 | 2.69 | 0.07 | 0.8731 |
| 2 | 2.59 | 2.54 | 0.05 | 0.4322 |
| 3 | 2.39 | 2.37 | 0.04 | 0.6515 |
| 4 | 2.19 | 2.22 | 0.07 | 0.7097 |
| 5 | 2.04 | 2.09 | 0.07 | 0.6751 |
| 6 | 1.92 | 1.96 | 0.07 | 0.7181 |
| 7 | 1.82 | 1.87 | 0.06 | 0.4842 |
| 8 | 1.73 | 1.81 | 0.05 | 0.3423 |
| Total abnormal fecal scores (abnormal >2 fecal score) | | | | |
| 1 | 6.25 | 6.47 | 0.16 | 0.3324 |
| 2 | 5.29 | 4.53 | 0.35 | 0.1235 |
| 3 | 1.21 | 1.43 | 0.38 | 0.6684 |
| 4 | 0.62 | 1.17 | 0.49 | 0.4137 |
| 5 | 0.46 | 0.80 | 0.37 | 0.5130 |
| 6 | 0.21 | 0.34 | 0.22 | 0.6579 |
| 7 | 0.09 | 0.57 | 0.15 | 0.0263 |
| 8 | 0.20 | 0.22 | 0.14 | 0.9161 |
| Total abnormal fecal scores cumulative (abnormal >2 fecal score) | | | | |
| 1 | 6.25 | 6.47 | 0.16 | 0.3324 |
| 2 | 11.53 | 11.00 | 0.43 | 0.3703 |
| 3 | 12.74 | 12.43 | 0.68 | 0.7413 |
| 4 | 13.37 | 13.58 | 0.87 | 0.8615 |
| 5 | 13.78 | 14.43 | 1.05 | 0.6584 |
| 6 | 13.98 | 14.77 | 1.18 | 0.6334 |
| 7 | 14.08 | 15.34 | 1.19 | 0.4487 |
| 8 | 14.28 | 15.56 | 1.19 | 0.4435 |

TABLE III-continued

Body condition score changes (1 = thin, 5 = obese)

| | | | | |
|---|---|---|---|---|
| Initial Score | 2.07 | 1.98 | 0.05 | 0.1431 |
| Change 0 to 2 wk | −0.14 | −0.00 | 0.05 | 0.0484 |
| Change 0 to 4 wk | −0.15 | −0.01 | 0.05 | 0.0464 |
| Change 0 to 6 wk | 0.07 | 0.26 | 0.07 | 0.0596 |
| Change 0 to 8 wk | 0.41 | 0.53 | 0.09 | 0.3437 |
| Change 2 to 4 wk | −0.01 | −0.01 | 0.03 | 0.9513 |
| Change 4 to 6 wk | 0.21 | 0.27 | 0.05 | 0.4161 |
| Change 6 to 8 wk | 0.36 | 0.24 | 0.09 | 0.3287 |

Hip width changes, cm

| | | | | |
|---|---|---|---|---|
| Initial Width | 17.71 | 17.34 | 0.21 | 0.2027 |
| Change 0 to 2 wk | 0.01 | 0.50 | 0.10 | 0.0017 |
| Change 0 to 4 wk | 0.74 | 1.45 | 0.12 | 0.0001 |
| Change 0 to 6 wk | 1.83 | 2.79 | 0.19 | 0.0006 |
| Change 0 to 8 wk | 3.08 | 4.20 | 0.22 | 0.0009 |
| Change 2 to 4 wk | 0.73 | 0.95 | 0.09 | 0.0849 |
| Change 4 to 6 wk | 1.09 | 1.34 | 0.14 | 0.2159 |
| Change 6 to 8 wk | 1.26 | 1.40 | 0.13 | 0.4445 |

[a] When P Values were lower than .1, treatment C was different than treatments A and B.

TABLE IV

LS Treatment means by week for calves fed two different electrolytes in Trial 3.

| | B) Elec B | C) Elec C | SEM | P-Value[a] |
|---|---|---|---|---|
| | Average daily gain, g | | | |
| 1 | −25.89 | 147.46 | 46.4 | 0.0095 |
| 2 | 205.50 | 124.83 | 35.8 | 0.1076 |
| 3 | 426.52 | 415.24 | 33.7 | 0.8075 |
| 4 | 515.62 | 471.97 | 41.8 | 0.4486 |
| 5 | 573.91 | 635.41 | 42.4 | 0.2951 |
| 6 | 582.96 | 617.47 | 46.0 | 0.5858 |
| 7 | 811.65 | 853.23 | 54.7 | 0.5806 |
| 8 | 927.45 | 1,080.02 | 61.8 | 0.0788 |
| | Average daily gain cumulative, g | | | |
| 1 | −25.89 | 147.46 | 46.4 | 0.0095 |
| 2 | 89.80 | 136.15 | 30.5 | 0.2724 |
| 3 | 202.04 | 229.18 | 24.1 | 0.4143 |
| 4 | 280.44 | 289.87 | 22.3 | 0.7579 |
| 5 | 339.13 | 358.98 | 20.6 | 0.4853 |
| 6 | 379.77 | 402.06 | 21.3 | 0.4486 |
| 7 | 441.47 | 466.52 | 24.0 | 0.4487 |
| 8 | 502.21 | 543.20 | 24.9 | 0.2352 |
| | Cumulative average daily starter intake, g | | | |
| 1 | 36.41 | 23.68 | 7.02 | 0.1924 |
| 2 | 107.62 | 73.85 | 13.6 | 0.0772 |
| 3 | 191.37 | 149.13 | 17.6 | 0.0876 |
| 4 | 276.31 | 237.72 | 21.5 | 0.1957 |
| 5 | 361.83 | 327.16 | 24.0 | 0.2964 |
| 6 | 455.65 | 425.99 | 27.3 | 0.4307 |
| 7 | 628.20 | 609.92 | 33.1 | 0.6882 |
| 8 | 811.65 | 806.99 | 39.5 | 0.9316 |
| | Weekly starter intake, g | | | |
| 1 | 254.85 | 165.75 | 49.2 | 0.1924 |
| 2 | 1,251.78 | 868.11 | 147 | 0.0639 |
| 3 | 2,512.24 | 2,097.93 | 209 | 0.1557 |
| 4 | 3,717.94 | 3,524.42 | 277 | 0.6123 |
| 5 | 4,927.25 | 4,794.40 | 328 | 0.7685 |
| 6 | 6,473.23 | 6,441.07 | 375 | 0.9503 |
| 7 | 11,644.35 | 11,994.38 | 574 | 0.6577 |
| 8 | 14,670.71 | 15,305.60 | 688 | 0.5029 |
| | Starter intake cumlative, g | | | |
| 1 | 254.85 | 165.75 | 49.2 | 0.1924 |
| 2 | 1,506.63 | 1,033.85 | 191 | 0.0772 |
| 3 | 4,018.87 | 3,131.78 | 370 | 0.0876 |
| 4 | 7,736.80 | 6,656.20 | 601 | 0.1957 |
| 5 | 12,664.06 | 11,450.59 | 839 | 0.2964 |

TABLE IV-continued

LS Treatment means by week for calves fed two different electrolytes in Trial 3.

| | B) Elec B | C) Elec C | SEM | P-Value[a] |
|---|---|---|---|---|
| 6 | 19,137.29 | 17,891.66 | 1145 | 0.4307 |
| 7 | 30,781.64 | 29,886.04 | 1622 | 0.6882 |
| 8 | 45,452.35 | 45,191.64 | 2212 | 0.9316 |
| | Feed efficiency cumulative (Starter and Milk Replacer/Gain) | | | |
| 1 | −1.74 | −1.59 | 2.70 | 0.9673 |
| 2 | 10.75 | 1.47 | 4.19 | 0.1129 |
| 3 | 3.34 | 3.01 | 0.32 | 0.4415 |
| 4 | 2.55 | 2.42 | 0.14 | 0.5083 |
| 5 | 2.32 | 2.12 | 0.08 | 0.0658 |
| 6 | 2.30 | 2.12 | 0.07 | 0.0628 |
| 7 | 2.29 | 2.13 | 0.06 | 0.0484 |
| 8 | 2.31 | 2.12 | 0.05 | 0.0093 |
| | Weekly medical days | | | |
| 1 | 4.27 | 4.89 | 0.18 | 0.0189 |
| 2 | 0.60 | 1.17 | 0.27 | 0.1331 |
| 3 | 0.63 | 1.00 | 0.32 | 0.4177 |
| 4 | 0.60 | 0.13 | 0.19 | 0.0712 |
| 5 | 0.75 | 0.43 | 0.22 | 0.2862 |
| 6 | 0.38 | 0.27 | 0.20 | 0.6887 |
| 7 | 0.28 | 0.18 | 0.16 | 0.6854 |
| 8 | 0.23 | 0.45 | 0.18 | 0.3646 |
| | Fecal score (1 = normal, 5 = watery) | | | |
| 1 | 2.41 | 2.51 | 0.04 | 0.0593 |
| 2 | 1.88 | 2.06 | 0.08 | 0.1081 |
| 3 | 1.49 | 1.60 | 0.08 | 0.3071 |
| 4 | 1.14 | 1.19 | 0.05 | 0.4283 |
| 5 | 1.15 | 1.11 | 0.06 | 0.6539 |
| 6 | 1.12 | 1.19 | 0.06 | 0.3421 |
| 7 | 1.08 | 1.21 | 0.05 | 0.0816 |
| 8 | 1.16 | 1.18 | 0.07 | 0.8054 |
| | Weekly medical days cumulative | | | |
| 1 | 4.27 | 4.89 | 0.18 | 0.0189 |
| 2 | 4.88 | 6.05 | 0.37 | 0.0261 |
| 3 | 5.51 | 7.05 | 0.50 | 0.0296 |
| 4 | 6.11 | 7.18 | 0.55 | 0.1642 |
| 5 | 6.86 | 7.61 | 0.57 | 0.3460 |
| 6 | 7.24 | 7.88 | 0.63 | 0.4622 |
| 7 | 7.51 | 8.06 | 0.67 | 0.5552 |
| 8 | 7.74 | 8.51 | 0.75 | 0.4555 |
| | Fecal score cumulative (1 = normal, 5 = watery) | | | |
| 1 | 2.41 | 2.51 | 0.04 | 0.0593 |
| 2 | 2.14 | 2.29 | 0.05 | 0.0293 |
| 3 | 1.92 | 2.06 | 0.05 | 0.0415 |
| 4 | 1.73 | 1.84 | 0.04 | 0.0428 |
| 5 | 1.61 | 1.70 | 0.04 | 0.0976 |
| 6 | 1.53 | 1.61 | 0.04 | 0.0930 |
| 7 | 1.46 | 1.55 | 0.03 | 0.0601 |
| 8 | 1.43 | 1.51 | 0.03 | 0.0544 |
| | Total abnormal fecal scores (abnormal >2 fecal score) | | | |
| 1 | 4.13 | 5.18 | 0.33 | 0.0242 |
| 2 | 1.53 | 2.75 | 0.47 | 0.0671 |
| 3 | 0.75 | 0.97 | 0.32 | 0.6094 |
| 4 | 0.14 | 0.26 | 0.15 | 0.5620 |
| 5 | 0.34 | 0.13 | 0.16 | 0.3423 |
| 6 | 0.21 | 0.20 | 0.14 | 0.9848 |
| 7 | 0.00 | 0.00 | — | — |
| 8 | 0.10 | 0.07 | 0.09 | 0.8244 |
| | Total abnormal fecal scores cumulative (abnormal >2 fecal score) | | | |
| 1 | 4.13 | 5.18 | 0.33 | 0.0242 |
| 2 | 5.66 | 7.93 | 0.60 | 0.0091 |
| 3 | 6.40 | 8.89 | 0.75 | 0.0207 |
| 4 | 6.55 | 9.15 | 0.82 | 0.0257 |
| 5 | 6.89 | 9.28 | 0.90 | 0.0585 |
| 6 | 7.10 | 9.49 | 0.94 | 0.0709 |
| 7 | 7.10 | 9.49 | 0.94 | 0.0709 |
| 8 | 7.20 | 9.56 | 0.93 | 0.0710 |

TABLE IV-continued

LS Treatment means by week for calves fed two different electrolytes in Trial 3.

|  | B) Elec B | C) Elec C | SEM | P-Value[a] |
|---|---|---|---|---|
| Body condition score changes (1 = thin, 5 = obese) | | | | |
| Initial Score | 2.07 | 2.04 | 0.05 | 0.6504 |
| Change 0 to 2 wk | 0.08 | 0.07 | 0.04 | 0.9544 |
| Change 0 to 4 wk | 0.18 | 0.29 | 0.05 | 0.1375 |
| Change 0 to 6 wk | 0.40 | 0.49 | 0.05 | 0.2061 |
| Change 0 to 8 wk | 0.62 | 0.69 | 0.05 | 0.3832 |
| Change 2 to 4 wk | 0.10 | 0.21 | 0.05 | 0.0913 |
| Change 4 to 6 wk | 0.22 | 0.20 | 0.04 | 0.7238 |
| Change 6 to 8 wk | 0.22 | 0.20 | 0.03 | 0.5524 |
| Hip width changes, cm | | | | |
| Initial Width | 17.75 | 17.51 | 0.22 | 0.4372 |
| Change 0 to 2 wk | 0.45 | 0.61 | 0.10 | 0.2489 |
| Change 0 to 4 wk | 1.26 | 1.31 | 0.11 | 0.7208 |
| Change 0 to 6 wk | 2.30 | 2.54 | 0.14 | 0.2174 |
| Change 0 to 8 wk | 3.98 | 4.05 | 0.17 | 0.7496 |
| Change 2 to 4 wk | 0.81 | 0.70 | 0.09 | 0.3947 |
| Change 4 to 6 wk | 1.04 | 1.23 | 0.09 | 0.1491 |
| Change 6 to 8 wk | 1.67 | 1.51 | 0.10 | 0.2491 |

[a]When P Values were lower than .1, treatment C was different than treatments A and B.

TABLE V

LS Treatment means by week for calves fed two different electrolytes in Trial 4.

|  | B) Elec B | C) Elec C | SEM | P-Value[a] |
|---|---|---|---|---|
| Average daily gain, g | | | | |
| 1 | 91.74 | 278.94 | 39.7 | 0.0016 |
| 2 | 230.32 | 178.41 | 35.1 | 0.2979 |
| 3 | 377.07 | 398.99 | 27.0 | 0.5659 |
| 4 | 548.26 | 538.66 | 40.6 | 0.8670 |
| 5 | 640.28 | 655.30 | 40.6 | 0.7936 |
| 6 | 582.43 | 534.16 | 39.5 | 0.3893 |
| 7 | 658.42 | 661.42 | 55.8 | 0.9696 |
| 8 | 1,049.46 | 1,015.41 | 68.2 | 0.7239 |
| Average daily gain cumulative, g | | | | |
| 1 | 91.74 | 278.94 | 39.7 | 0.0016 |
| 2 | 161.03 | 228.68 | 23.9 | 0.0499 |
| 3 | 233.04 | 285.45 | 20.5 | 0.0750 |
| 4 | 311.85 | 348.75 | 21.6 | 0.2311 |
| 5 | 377.53 | 410.06 | 23.1 | 0.3225 |
| 6 | 411.68 | 430.74 | 23.3 | 0.5636 |
| 7 | 446.93 | 463.70 | 24.1 | 0.6235 |
| 8 | 522.25 | 532.66 | 24.9 | 0.7678 |
| Average daily starter intake cumulative, g | | | | |
| 1 | 31.49 | 30.51 | 6.32 | 0.9132 |
| 2 | 91.55 | 86.27 | 11.9 | 0.7534 |
| 3 | 172.63 | 161.98 | 16.7 | 0.6526 |
| 4 | 247.04 | 246.46 | 22.4 | 0.9855 |
| 5 | 329.69 | 332.13 | 27.9 | 0.9506 |
| 6 | 416.81 | 411.80 | 32.6 | 0.9133 |
| 7 | 572.62 | 557.78 | 39.9 | 0.7922 |
| 8 | 742.70 | 728.39 | 46.0 | 0.8260 |
| Weekly starter intake, g | | | | |
| 1 | 220.41 | 213.59 | 44.2 | 0.9132 |
| 2 | 1,061.28 | 994.18 | 131 | 0.7169 |
| 3 | 2,343.58 | 2,193.83 | 195 | 0.5875 |
| 4 | 3,291.82 | 3,499.41 | 300 | 0.6253 |
| 5 | 4,622.24 | 4,723.68 | 383 | 0.8514 |
| 6 | 5,966.73 | 5,670.92 | 446 | 0.6390 |
| 7 | 10,552.50 | 10,035.72 | 647 | 0.5724 |
| 8 | 13,532.45 | 13,458.68 | 708 | 0.9412 |
| Starter intake cumulative, g | | | | |
| 1 | 220.41 | 213.59 | 44.2 | 0.9132 |
| 2 | 1,281.69 | 1,207.77 | 166 | 0.7534 |
| 3 | 3,625.27 | 3,401.60 | 351 | 0.6526 |
| 4 | 6,917.09 | 6,901.01 | 627 | 0.9855 |
| 5 | 11,539.32 | 11,624.69 | 975 | 0.9506 |
| 6 | 17,506.06 | 17,295.61 | 1368 | 0.9133 |
| 7 | 28,058.55 | 27,331.33 | 1953 | 0.7922 |
| 8 | 41,591.01 | 40,790.01 | 2579 | 0.8260 |
| Feed efficiency cumulative (Starter and Milk Replacer/Gain) | | | | |
| 1 | 4.87 | 1.35 | 2.71 | 0.3589 |
| 2 | 2.46 | 1.42 | 0.90 | 0.4139 |
| 3 | 3.60 | 2.48 | 0.48 | 0.1090 |
| 4 | 2.43 | 2.22 | 0.16 | 0.3711 |
| 5 | 2.18 | 2.03 | 0.10 | 0.3208 |
| 6 | 2.15 | 2.07 | 0.08 | 0.5109 |
| 7 | 2.18 | 2.08 | 0.07 | 0.2861 |
| 8 | 2.09 | 2.02 | 0.06 | 0.4277 |
| Weekly medical days | | | | |
| 1 | 5.00 | 4.96 | 0.17 | 0.8699 |
| 2 | 0.27 | 0.41 | 0.18 | 0.5541 |
| 3 | 0.18 | 0.10 | 0.10 | 0.5918 |
| 4 | 0.54 | 0.04 | 0.15 | 0.0246 |
| 5 | 1.49 | 0.65 | 0.25 | 0.0208 |
| 6 | 0.11 | 0.41 | 0.14 | 0.1223 |
| 7 | 0.78 | 0.70 | 0.21 | 0.7705 |
| 8 | 0.23 | 0.13 | 0.10 | 0.4600 |
| Fecal score (1 = normal, 5 = watery) | | | | |
| 1 | 2.67 | 2.72 | 0.05 | 0.5186 |
| 2 | 2.24 | 2.20 | 0.05 | 0.6436 |
| 3 | 1.84 | 1.70 | 0.08 | 0.2246 |
| 4 | 1.65 | 1.57 | 0.10 | 0.6160 |
| 5 | 1.60 | 1.61 | 0.09 | 0.9313 |
| 6 | 1.12 | 1.13 | 0.03 | 0.8813 |
| 7 | 1.25 | 1.40 | 0.07 | 0.1385 |
| 8 | 1.20 | 1.18 | 0.05 | 0.7580 |
| Weekly medical days cumulative | | | | |
| 1 | 5.00 | 4.96 | 0.17 | 0.8699 |
| 2 | 5.27 | 5.37 | 0.19 | 0.6914 |
| 3 | 5.44 | 5.48 | 0.23 | 0.9127 |
| 4 | 5.98 | 5.52 | 0.26 | 0.2045 |
| 5 | 7.47 | 6.17 | 0.41 | 0.0270 |
| 6 | 7.58 | 6.58 | 0.44 | 0.1117 |
| 7 | 8.37 | 7.28 | 0.51 | 0.1381 |
| 8 | 8.60 | 7.41 | 0.51 | 0.1042 |
| Fecal score cumulative (1 = normal, 5 = watery) | | | | |
| 1 | 2.67 | 2.72 | 0.05 | 0.5186 |
| 2 | 2.45 | 2.46 | 0.04 | 0.9194 |
| 3 | 2.25 | 2.21 | 0.05 | 0.5606 |
| 4 | 2.10 | 2.05 | 0.06 | 0.5425 |
| 5 | 2.00 | 1.96 | 0.06 | 0.6592 |
| 6 | 1.85 | 1.82 | 0.05 | 0.6764 |
| 7 | 1.77 | 1.76 | 0.04 | 0.9699 |
| 8 | 1.70 | 1.69 | 0.04 | 0.9285 |
| Total abnormal fecal scores (abnormal >2 fecal score) | | | | |
| 1 | 6.03 | 6.53 | 0.27 | 0.1989 |
| 2 | 3.39 | 3.39 | 0.43 | 0.9995 |
| 3 | 0.74 | 0.21 | 0.22 | 0.0983 |
| 4 | 0.72 | 0.66 | 0.30 | 0.8851 |
| 5 | 0.72 | 0.71 | 0.27 | 0.9797 |
| 6 | 0.04 | 0.00 | 0.03 | 0.4110 |
| 7 | 0.55 | 0.42 | 0.23 | 0.6949 |
| 8 | 0.03 | 0.05 | 0.04 | 0.7976 |
| Total abnormal fecal scores cumulative (abnormal >2 fecal score) | | | | |
| 1 | 6.03 | 6.53 | 0.27 | 0.1989 |
| 2 | 9.42 | 9.92 | 0.56 | 0.5298 |
| 3 | 10.16 | 10.13 | 0.67 | 0.9720 |
| 4 | 10.89 | 10.79 | 0.83 | 0.9360 |

TABLE V-continued

LS Treatment means by week for calves fed two different electrolytes in Trial 4.

|  | B) Elec B | C) Elec C | SEM | P-Value[a] |
|---|---|---|---|---|
| 5 | 11.60 | 11.50 | 0.88 | 0.9333 |
| 6 | 11.64 | 11.50 | 0.88 | 0.9110 |
| 7 | 12.19 | 11.92 | 0.86 | 0.8262 |
| 8 | 12.22 | 11.97 | 0.86 | 0.8370 |
| Body condition score changes (1 = thin, 5 = obese) | | | | |
| Initial Score | 2.09 | 2.05 | 0.03 | 0.4633 |
| Change 0 to 2 wk | 0.01 | 0.04 | 0.03 | 0.5396 |
| Change 0 to 4 wk | 0.22 | 0.30 | 0.03 | 0.0804 |
| Change 0 to 6 wk | 0.38 | 0.37 | 0.05 | 0.9035 |
| Change 0 to 8 wk | 0.57 | 0.59 | 0.05 | 0.7980 |
| Change 2 to 4 wk | 0.21 | 0.26 | 0.03 | 0.2482 |
| Change 4 to 6 wk | 0.16 | 0.07 | 0.03 | 0.0677 |
| Change 6 to 8 wk | 0.20 | 0.22 | 0.03 | 0.5743 |
| Hip width changes, cm | | | | |
| Initial Width | 17.78 | 17.63 | 0.19 | 0.5810 |
| Change 0 to 2 wk | 0.20 | 0.33 | 0.08 | 0.2591 |
| Change 0 to 4 wk | 1.16 | 1.26 | 0.11 | 0.5238 |
| Change 0 to 6 wk | 2.19 | 2.39 | 0.15 | 0.3381 |
| Change 0 to 8 wk | 3.67 | 3.75 | 0.21 | 0.7758 |
| Change 2 to 4 wk | 0.96 | 0.92 | 0.08 | 0.7362 |
| Change 4 to 6 wk | 1.03 | 1.14 | 0.09 | 0.3941 |
| Change 6 to 8 wk | 1.48 | 1.36 | 0.11 | 0.4559 |

[a]When P Values were lower than .1, treatment C was different than treatments A and B.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. A method for treating or reducing the likelihood of dehydration in a neonatal bovine mammal, said method comprising the steps of:
    providing a physiological composition comprising a source of nutrients, said nutrients including in an effective amount to treat or reduce the likelihood of dehydration in said neonatal bovine mammal;
    administering to said neonatal bovine mammal said physiological composition wherein said source of nutrients comprises crude protein from a milk protein source and electrolytes, wherein said nutrients include dextrans having at least two different saccharides; and
    said dextrans including a majority of maltodextrins relative to any other saccharide therein;
    providing enough energy and protein to maintain a body weight and growth of said neonatal bovine mammal;
    wherein an amount of said dextrans is greater than an amount of any other of said nutrients.

2. The method of claim 1, wherein said source of nutrients are prepackaged in a sealed container, said method further comprising the step of rehydrating said physiological composition from said prepackaged source of nutrients prior to administering said composition to said neonatal bovine mammal.

3. The method of claim 2, wherein said step of rehydrating said physiological composition comprises adding about 0.45 to 0.55 pounds of said physiological composition to about two quarts of water.

4. The method of claim 3, wherein said physiological composition is added to about one quart of water to form a first solution and said first solution is subsequently diluted with about one quart of water to form a second solution, said second solution being administered to said neonatal bovine mammal about three or more times in a 24-hour period.

5. The method of claim 1, wherein said source of nutrients comprises:
    about 50 to 60% dextrans;
    about 10 to 20% bicarbonate of soda;
    about 1 to 10% sodium; and
    about 1 to 10% potassium.

6. The method of claim 5, wherein said dextrans includes a mixture of maltodextrins and dextrose.

7. The method of claim 6, wherein said mixture of maltodextrins and dextrose includes about 35 to 45% maltodextrins and about 10 to 20% dextrose.

8. The method of claim 1, further comprising at least one agent selected from the group consisting of whey protein concentrate, microbial blend, emulsifier, or anti-caking agent, and one or more amino acids, artificial flavors, or vitamins.

9. The method of claim 1, wherein said neonatal bovine mammal is a calf.

10. The method of claim 9, wherein said calf is about three months of age or less.

11. The method of claim 2, wherein said source of nutrients are sealed together in a single container.

* * * * *